US009629789B2

(12) United States Patent
Faryniarz et al.

(10) Patent No.: US 9,629,789 B2
(45) Date of Patent: Apr. 25, 2017

(54) ROSACEA TREATMENTS USING POLYMETAL COMPLEXES

(71) Applicant: Obagi Medical Products, Inc., Bridgewater, NJ (US)

(72) Inventors: Joseph R. Faryniarz, Middlebury, CT (US); Jose E Ramirez, Trumbull, CT (US); Hovig Ounian, Denton, TX (US)

(73) Assignee: Obagi Medical Products, Inc., Bridgewater, NJ (US)

( * ) Notice: Subject to any disclaimer, the term of this patent is extended or adjusted under 35 U.S.C. 154(b) by 0 days.

(21) Appl. No.: 14/026,592

(22) Filed: Sep. 13, 2013

(65) Prior Publication Data

US 2014/0134119 A1 May 15, 2014

Related U.S. Application Data

(63) Continuation of application No. 12/831,424, filed on Jul. 7, 2010, now abandoned.

(60) Provisional application No. 61/225,041, filed on Jul. 13, 2009.

(51) Int. Cl.

| | | |
|---|---|---|
| *A61K 8/00* | (2006.01) | |
| *A61K 8/67* | (2006.01) | |
| *A61K 8/362* | (2006.01) | |
| *A61K 31/315* | (2006.01) | |
| *A61K 31/415* | (2006.01) | |
| *A61K 31/59* | (2006.01) | |
| *A61K 33/30* | (2006.01) | |
| *A61Q 17/04* | (2006.01) | |
| *A61Q 19/00* | (2006.01) | |
| *A61Q 19/10* | (2006.01) | |
| *A61K 8/27* | (2006.01) | |
| *A61K 31/07* | (2006.01) | |
| *A61K 31/235* | (2006.01) | |
| *A61K 31/4164* | (2006.01) | |
| *A61K 31/60* | (2006.01) | |
| *A61K 45/06* | (2006.01) | |

(52) U.S. Cl.
CPC ............ *A61K 8/67* (2013.01); *A61K 8/27* (2013.01); *A61K 8/362* (2013.01); *A61K 8/671* (2013.01); *A61K 31/07* (2013.01); *A61K 31/235* (2013.01); *A61K 31/315* (2013.01); *A61K 31/415* (2013.01); *A61K 31/4164* (2013.01); *A61K 31/59* (2013.01); *A61K 31/60* (2013.01); *A61K 33/30* (2013.01); *A61K 45/06* (2013.01); *A61Q 17/04* (2013.01); *A61Q 19/00* (2013.01); *A61Q 19/10* (2013.01); *A61K 2800/88* (2013.01); *A61K 2800/884* (2013.01)

(58) Field of Classification Search
CPC ............ A61K 31/137; A61K 31/327; A61K 31/4174; A61K 31/60; A61K 33/00; A61K 36/03; A61K 36/05; A61K 36/062; A61K 36/19; A61K 36/185; A61K 36/22; A61K 36/23; A61K 36/25; A61K 36/28; A61Q 19/06; A61Q 19/10; A61Q 5/02; A61Q 5/12; C07F 3/003
See application file for complete search history.

(56) References Cited

U.S. PATENT DOCUMENTS

| | | | |
|---|---|---|---|
| 7,258,875 B2 | 8/2007 | Chiou | |
| 7,687,650 B2 | 3/2010 | Ramirez et al. | |
| 7,812,049 B2 * | 10/2010 | Shanler et al. | 514/401 |
| 7,897,800 B2 | 3/2011 | Ramirez et al. | |
| 2004/0057972 A2 | 3/2004 | Shacknai et al. | |
| 2004/0208902 A1 * | 10/2004 | Gupta | 424/401 |
| 2006/0024339 A1 * | 2/2006 | Murad | 424/401 |
| 2007/0184017 A1 | 8/2007 | Faryniarz et al. | |
| 2007/0191620 A1 * | 8/2007 | Ramirez et al. | 556/114 |
| 2007/0203354 A1 | 8/2007 | Ramirez et al. | |
| 2008/0081077 A1 | 4/2008 | Faryniarz et al. | |
| 2008/0194664 A1 | 8/2008 | Kaoukhov et al. | |
| 2009/0176876 A1 | 7/2009 | Ramirez et al. | |
| 2010/0144870 A1 | 6/2010 | Ramirez et al. | |
| 2010/0247628 A1 | 9/2010 | Dorogi et al. | |

FOREIGN PATENT DOCUMENTS

| | | |
|---|---|---|
| EP | 2 087 880 A2 | 8/2009 |
| WO | 2006/131653 A1 | 12/2006 |
| WO | 2007/089267 A1 | 8/2007 |

OTHER PUBLICATIONS

ZenMed, How does this system treat rosacea, Retrieved online [Dec. 15, 2012], Retrieved from URL:<http://web.archive.org/web/20080817065108/http://zenmed.com/skincare/rosacea/thesystem.aspx>.*
Culp et al., Rosacea: A Review, P&T, vol. 34, No. 1, pp. 38-45.*
Redness Therapy Regimen, Retrieved online from URL:<http://www.murad.com/redness-therapy>.*
CLINIQUE: "Redness Solutions Redness Regime" (Apr. 3, 2008) Retrieved from the Internet: http://web.archive.org/web/20080403232732/http://www.clinique.co.uk/templates/products/sp_nonshaded.tmpl?CATEGORY_ID=CAT10014&PRODUCT_ID=PROD89685 [retrieved on Mar. 5, 2010]. 1 page.
Sephora: "Clinique Redness Solutions Kit" (no publication date provided by Sephora) Retrieved from the Internet: http://www.sephora.com/redness-solutions-kit-P209119 [retrieved on Sep. 2, 2013]. 3 pages.
Webster, G.F., "Treatment of Rosecea," Seminars in Cutaneous Medicine and Surgery, W.B. Saunders, Philadelphia, US, vol. 20, No. 3, (Sep. 1, 2001) p. 207/208.

(Continued)

*Primary Examiner* — Nannette Holloman
(74) *Attorney, Agent, or Firm* — Kilpatrick Townsend & Stockton LLP

(57) ABSTRACT

Described herein are novel methods for the treatment of rosacea which include the step of applying of a composition containing a polymetal complex to an area of the skin afflicted with rosacea and novel regimens using such compounds.

20 Claims, No Drawings

(56) References Cited

OTHER PUBLICATIONS

ZENMED: "Rosacea Treatment Systems from ZENMED" (Jul. 29, 2008) Retrieved from the Internet: http://web.archive.org/web/20080729052452/zenmed.com/skincare/rosacea/ [retrieved on Mar. 5, 2010]. 4 pages.

Bucheli, Peter et al., "Biomolecular and Clinical Aspects of Chinese Wolfberry," Herbal Medicine Biomolecular and Clinical Aspects, 2nd Ed., Chapter 14, Eds. Benzie and Wachtel-Galor, CRC Press, Boca Raton, 2011, pp. 289-314.

* cited by examiner

ROSACEA TREATMENTS USING POLYMETAL COMPLEXES

CROSS REFERENCE TO RELATED APPLICATION

This application claims priority to and the benefit of U.S. Provisional Application Ser. No. 61/225,041 filed on Jul. 13, 2009, the entire contents of which are incorporated herein by reference.

TECHNICAL FIELD

The present disclosure relates to compositions and methods for the treatment of rosacea.

BACKGROUND

Rosacea is a chronic inflammation disease that occurs with mostly fair skin people. By some recent estimates rosacea afflicts 13 million Americans. It usually first appears as subtle reddening on the face. Over time this may develop into inflammation, be accompanied by skin eruptions, and in the appearance of red lines which result from swollen or damaged veins and capillary blood vessels immediately under the surface of the skin.

There is no single test to determine whether someone has rosacea. The diagnosis is usually made based on a visual examination and from identifying a number of symptoms, such as: flushing or blushing that occurs easily and often and lasts longer than normal; erythema (i.e., rashes and redness on part or all of the face); burning or stinging sensations; papules, or pustules; rhinophyma; and/or telangiectasis caused as a result of capillary blood vessels in the face becoming enlarged or damaged. Symptoms are often aggravated by sun exposure, changes or extremes in temperature, wind, and consumption of certain foods (including spicy foods, caffeine & alcohol).

Rosacea is generally categorized into four stages. Stage one is characterized by flushing or redness (known as erythema) that lasts for hours or days. Red lines (a condition known as telangiectases) may appear. Stages two and Three, Papulopustular and Phymatous, are characterized by skin eruptions (nodules, papules pustules). Symptoms may spread from the face to other parts of the body such as the scalp, neck & chest. Stage four, Ocular, is characterized by large nodules appearing, sever inflammation, facial pain, swelling and burning. Rhinophyma the bulbous enlargement of the nose may also be present with some subjects.

The exact cause of rosacea is still largely unknown, however the symptoms are reasonably well understood as are a variety of lifestyle factors (such as particular foods and activities) that are known to trigger outbreaks in people that have the disease. Although there is not yet a cure for rosacea, a combination of treatment of the symptoms and lifestyle changes to avoid these triggers can greatly reduce the negative impacts of rosacea.

In general, the treatment is aimed at the control of redness, inflammation, and skin eruptions. Treatment is necessary to prevent permanent damage and progression of the symptoms. In more severe cases, once a diagnosis of rosacea has been made a dermatologist will prescribed a combination of oral antibiotics and the use of antibiotic gel as initial treatment. The oral antibiotics (e.g., minocycline or erythromycin) will bring the condition under control (reducing redness and the formation of papules and pustules), then the topical treatments will be used to keep the symptoms under control. Since rosacea cannot be cured it will often be necessary to continue with topical treatment (and modification of lifestyle factors) even after symptoms have been reduced or have disappeared. In addition, laser treatments may be employed to seal the broken vessels and prevent blood flow to the surface off the skin. Alternatively, mixed intense pulse light (IPL) may be employed to treat Rosacea symptoms. Light pulse therapy works by sending light energy through the outer skin, concentrating on the dermal layer just below and attacks the problem from the inside, stimulating growth of collagen.

There is thus a continuing need for improved and effectual treatments for rosacea.

SUMMARY

Methods for treating skin afflicted with rosacea are described herein and include the step of applying a redness-reducing amount of a polymetal complex to at least a portion of the afflicted skin. In embodiments, the polymetal complex may be combined with a moisturizer. In addition, the methods may further include the sequential application of at least one of the following: an antibiotic or antimicrobial cleanser, a protective composition, an anti-parasitic product and various combinations thereof.

In some embodiments, regimens for treatment of rosacea in accordance with the present disclosure include sequential application of at least a) an antimicrobial cleanser; b) a moisturizer with a polymetal complex; and c) a protective composition. Depending on the severity of the rosacea, additional components may be applied such as anti-parasitic compounds, benzoyl peroxide, retinoids, and/or antibiotics.

In other embodiments, regimens for treatment of rosacea in accordance with the present disclosure include sequential application of at least a) a composition containing a polymetal complex; optionally b) a composition containing metronidazole; c) an anti-redness composition; and, optionally d) a protective composition.

In addition, kits for treating rosacea are described which include the polymetal complex and at least one of the following: a antimicrobial cleanser, a composition containing metronidazole, an anti-redness composition, a protective composition, a composition containing an anti-parasitic compound, a composition containing benzoyl peroxide, a composition containing a retinoid, and/or a composition containing an antibiotic.

DETAILED DESCRIPTION OF PREFERRED EMBODIMENTS

The present disclosure describes methods for treating skin afflicted with rosacea which include the step of applying a redness-reducing amount of a polymetal complex to at least a portion of the afflicted skin. In embodiments, the polymetal complex, e.g., Cu/Zn malonate, is combined with a moisturizer and applied to the afflicted skin. The polymetal complex moisturizer used in the present regimens improves capillary elasticity.

The polymetal complex can be the reaction product of a polyfunctional compound with two or more coordination elements. The preparation of reaction products of polyfunctional compounds with two or more coordination elements and compositions containing such reaction products are described. In embodiments, the resulting polymetal complex includes a first metal ion, a second metal ion that is different from the first metal ion and a central bridging unit linking the first and second metal ions, the central bridging unit being derived from a polyfunctional compound of the type described herein.

The polyfunctional compound can be any compound that contains at least two functional groups that may complex with metal cations in solution. Among the functional groups that may be present include carboxylic acid groups and amino groups. Suitable polyfunctional compounds include, but are not limited to polyfunctional acids, polyfunctional amines and amino acids. Other suitable polyfunctional compounds will be readily envisioned by those skilled in the art reading the present disclosure. It should of course be understood that mixtures of polyfunctional compounds may be used.

Polyfunctional acids are primarily monomeric compositions having two or more carboxylic acid groups. Non-limiting examples of polyfunctional acids include maleic acid, fumaric acid, citraconic acid, itaconic acid, glutaconic acid, phthalic acid, isophthalic acid, terephthalic acid, cyclohexane dicarboxylic acid, citric acid, succinic acid, adipic acid, sebacic acid, azealic acid, malonic acid, dodecanedioic acid, 1,18-octadecanedioic acid, dimer acids (prepared from a mono-, di- or triunsaturated fatty acid, acid wax, acid anhydride grafted wax, or other suitable polycarboxylic acid reacting compound), alkenyl succinic acids (such as n-dodecenylsuccinic acid, docecylcucinic acid and octadecenylsuccinic acid). Polysaccharides having two or more carboxylic groups can be used as the polyfunctional acid compound. Thus, for example, hyaluronic acid may be used as the polyfunctional compound. The polyfunctional acid can be present in acidic form, anhydride form, salt form, or mixtures thereof. Any derivative of any polyfunctional acid can be used provided the derivative still contains two carboxylic acid groups. In embodiments, the polyfunctional acid chosen as the polyfunctional compound contains exactly two carboxylic acid groups.

Amino acids may also be used as the polyfunctional compound. Amino acids are known to those skilled in the art and include at least a carboxylic acid functionality and an amino functionality. In embodiments, the amino acid chosen as the polyfunctional compound contains two carboxylic acid groups. Suitable amino acids include naturally occurring amino acids and synthetic amino acids. Non-limiting examples of amino acids include, but are not limited to: aminopolycarboxylic acids (e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid); amino acid amides such as glutamine and asparagine; polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid; other basic amino acid residues such as histidine; diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid; imino acids such as proline, hydroxyproline, allohydroxyproline, γ-methylproline, pipecolic acid, 5-hydroxypipecolic acid, and azetidine-2-carboxylic acid; mono- or di-alkyl (typically $C_1$-$C_8$ branched or normal) amino acids such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, aaminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid; β-phenylserinyl; aliphatic α-amino-β-hydroxy acids such as serine, β-hydroxyleucine, β-hydroxynorleucine, β-hydroxynorvaline, and α-amino-β-hydroxystearic acid; α-Amino, α-, γ-, δ- or ε-hydroxy acids such as homoserine, γ-hydroxynorvaline, δ-hydroxynorvaline and epsilon-hydroxynorleucine residues; canavine and canaline; γ-hydroxyornithine; 2.hexosaminic acids such as D-glucosaminic acid or D-galactosaminic acid; α-Amino-β-thiols such as penicillamine, β-thiolnorvaline or β-thiolbutyrine; other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine; phenylalanine, tryptophan and ring-substituted α amino acids such as the phenyl- or cyclohexylamino acids α-aminophenylacetic acid, aaminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dicloro, o-, m- or p-methyl-, 2,4,6-trimethyl-, 2-ethoxy-5-nitro-, 2-hydroxy-5-nitro- and p-nitrophenylalanine); furyl-, thienyl-, pyridyl-, pyrimidinyl-, purinyl- or naphthylalanines; and tryptophan analogues and derivatives including kynurenine, 3-hydroxykynurenine, 2-hydroxytryptophan and 4-carboxytryptophan; α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine. glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid. Polyaminoacids may also be used provided they form complexes with the coordination elements employed.

The polyfunctional compound is reacted with two or more coordination elements. The coordination elements can be chosen from the elements listed in Groups IIIA to VIIIA, Groups IB to IIIB, of periods 4 and 5 and aluminum in Group IIIB, period 3 of The Periodic Table of the Elements. Suitable non-limiting examples of elements listed in group IB of The Periodic Table of Elements include copper, silver, and gold. Suitable non-limiting examples of coordination elements include aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium. Tin may also be used. Those skilled in the art will readily envision suitable compounds for providing the coordination elements in solution. In embodiments, the coordination element is provided for the reaction as a basic salt that can participate in an acid-base reaction with a polyfunctional compound containing two carboxylic acid groups.

In embodiments, the polymetal complex is a copper-zinc malonate. Copper-zinc malonates may be one or more ionic compounds formed by joining one or more independent copper molecules or ions and one or more independent zinc molecules or ions to a central unit by ionic bonds. For example, the copper-zinc malonate may be in the form of a trinuclear cation, where structurally independent copper and zinc hydrates are bridged by a central unit such as an octahedral diaquadimalonatocopper (II) unit. However, various coordination modes are possible depending on the source of the copper and zinc and synthesis conditions. In embodiments, the central unit malonate ion may be a multi-membered ring such as eight-membered ring, six-membered ring, and four-membered metalocycle for bridging or chelating functions between the copper and zinc constituents. Accordingly, the crystal structures of copper-zinc malonates can be very diverse, from ionic to three-dimensional polymers. In embodiments, the copper-zinc malonates can be found in several hydrate, and polymorphic forms. Suitable copper-zinc malonate forms in accordance with the present disclosure include any salt formed from the neutralization of malonic acid by one or more copper containing molecules and one or more zinc containing molecules. In embodiments, copper and zinc are provided for the reaction as basic salts that can participate in an acid-base reaction with the two carboxylic acid groups present in malonic acid. Illustrative examples include salt formed by the neutralization of malonic acid by cupric carbonate ($CuCO_3 \cdot Cu(OH)_2$), and zinc carbonate ($3Zn(OH)_2 \cdot 2ZnCO_3$) in an aqueous solution.

It has been discovered that the compositions which contain the polymetal complex are useful in causing varying levels of vasoconstriction. Such an effect may be useful in treating rosacea. Moreover, the vasoconstrictive effect of the present compositions decrease the rate at which the body is able to clear the composition by local blood supply, thereby allowing the composition to remain at the site of application longer which increases the rate and depth of tissue penetration of the composition. In embodiments, the compositions of the present application may be combined with other vasoconstrictive agents to further enhance the effect of the polymetal complex. In still other embodiments, the compositions of the present application may be combined with vasodilating agents thereby decreasing the effect of the polymetal complex.

In embodiments, the polymetal complex may be combined with numerous ingredients to form products that can be applied to the skin of a person afflicted with rosacea. Such products may include a dermatologically or pharmaceutically acceptable carrier, vehicle or medium, for example, a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. In embodiments, compositions in accordance with the present disclosure can contain any ingredient conventionally used in cosmetics and/or dermatology. In embodiments, active ingredients may be formulated to provide crystals in solution, as well as solid forms. Methods of making the polymetal complex and formulating topical compositions containing them are described, for example, in published patent applications US-2007-0191620-A1, US-2007-0203354-A1, US-2007-0184017-A1, US-2007-0190190-A1, US-2008-0081077-A1, the entire contents of which are all incorporated herein by this reference.

In embodiments, products containing a polymetal complex in accordance with the present disclosure as an active ingredient can be in the form of solutions, emulsions (including microemulsions), suspensions, creams, lotions, gels, powders, or other typical solid or liquid compositions used for treatment of age related skin conditions. Such compositions may contain, in addition to the reaction product in accordance with this disclosure, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

As an illustrative example, products can be formulated to contain copper-zinc malonate in amounts from about 0.001 to about 5% by weight of the total composition. In embodiments, products can be formulated to contain copper-zinc malonate in an amount from about 0.05 to about 1.0% by weight of the total composition. In other embodiments, the amount of copper-zinc malonate is from about 0.1 to about 0.5% by weight of the total composition. Here, the copper-zinc malonate present may be in a pharmaceutically acceptable salt form. Other active ingredients may be provided in the formulations at the same concentrations.

Table A below provides an illustrative embodiment of a suitable composition containing a polymetal complex in accordance with thew present disclosure.

TABLE A

| Ingredient | Description (function) | Amount |
|---|---|---|
| Water Phase | | |
| Distilled Water | (solvent, humectant) | 69.4940 |
| PHENONIP | Phenoxyethanol, Methylparaben, Ethylparaben, Butylparaben, Propylparaben, Isobutylparaben (preservative) | 0.8000 |
| Propylene Glycol | (humectant) | 1.5000 |
| Glycerin | (humectant) | 2.5000 |
| Veegum Granules | Magnesium Aluminum Silicate (suspending agent) | 0.4000 |
| Keltrol CG | Xanthan Gum (viscosity building agent) | 0.6000 |
| Oil Phase | | |
| Finsolv TPP | C 12-15 Alkyl Benzoate; Dipropylene Glycol Dibenzoate, PPG-15 Stearyl Ether Benzoate, 50%/35%/15%; 2.25%/1.575%/0.75% (emollient) | 4.5000 |
| GE Silicone SF 1214 | Cyclopentasiloxane, Dimethicone, 80/20; 2.4%/0.6% (emollient) | 3.0000 |
| Gemseal 25 | C 13-15 Alkane (emollient) | 3.0000 |
| Pelemol OP | Ethylhexyl Palmitate (emollient) | 3.0000 |

TABLE A-continued

| Ingredient | Description (function) | Amount |
|---|---|---|
| Lipomulse 165 | Glyceryl Stearate, PEG-100 Stearate 2.475%/2.025% (emulsifier) | 4.5000 |
| Cetyl Alcohol | (thickener) | 0.5000 |
| Stearyl Alcohol | (thickener) | 1.5000 |
| GE Silicone 96-100 | Dimethicone (emollient) | 1.0000 |
| Abil Wax 9801 | Cetyl Dimethicone (emollient) | 0.1000 |
| Vitamin E Acetate | (vitamin) | 0.0500 |
| Engelhard Flamenco Satin Green P860 | Mica, Titanium Dioxide, Iron Oxides (pigments) | 0.0100 |
| Kobo BPD 500 | HDI/Trimethylol Hexyllactone Crosspolymer, Silica | 0.0100 |
| Presperse-Coverleaf AR-80 | Talc, Titanium Dioxide, Alumina, Silica (pigments) | 0.0010 |
| Copper-Zinc Malonate | (active) | 2.5000 |
| Sepigel 305 | Polyacrylamide, C 13-14 Isoparaffin, Laureth-7 (viscosifier/suspending agent) | 1.0000 |
| Extract Blend | Algae Extract, Glycyrrhiza Clabra Root Extract (antioxidants) | 0.0100 |
| Blueberry Fruit Extract | (antioxidants) | 0.025 |
| 8% NaOH Solution | (pH adjusting agent) | QS |
| 10% Malonic Acid Solution | | QS |

In embodiments, regimens for treatment of rosacea involve the sequential application of a series of products to the skin of a person afflicted with rosacea. The specific sequence of products applied in accordance with this disclosure will depend on the severity of the rosacea. The regimens for treating rosacea described herein include the application of a composition containing a polymetal complex and may further include the application of one or more of the following: an antibiotic or antimicrobial cleanser, a protective composition, an anti-parasitic product and various combinations thereof. In embodiments, the cleanser is applied to at least a portion of the afflicted skin prior to the application of the composition containing a polymetal complex. In embodiments, the protective composition is applied to at least a portion of the afflicted skin following the application of a composition containing a polymetal complex.

In still other embodiments, at least three products may be used to treat the afflicted skin. The three products applied may be an antimicrobial or antibiotic cleanser, a composition containing a polymetal complex, and a protective composition. In embodiments, the composition containing a polymetal complex contains Cu/Zn malonate.

The cleanser can be any non-soap cleanser that will remove dirt and oil from the skin. Suitable cleansers are commercially available and typically include a combination of anionic, cationic, amphoteric and/or non-ionic surfactants in an aqueous vehicle. The cleanser advantageously can include a combination of compounds to compensate for the well known fact that cleansing agents, by their very nature, are not always well tolerated by the skin. The oil-removal feature of a cleanser can result in drying of the skin, and even skin irritation. By incorporating various protective agents in the cleanser process the preferred cleanser overcomes shortcomings found in many alternative products. Thus, in one particularly useful embodiment the cleanser is a foaming gel cleanser that contains water, sodium lauroyl oat amino acids, cocamidopropyl betaine, sodium laureth sulfate, aloe barbadensis leaf juice, *medicago sative* (alfalfa) extract, borago officinalis extract, *chamomilla recutita* (matricaria) extract, sodium chloride, xanthan gum, saponins, phenoxyethanol, methylparaben, propylparaben, ethylparaben, butylparaben, fragrance, and color. In embodiments, the cleanser frees the skin of pollutants without damaging the skin's own natural moisture content. It also leaves all skin types clean and extremely soft to the touch.

In embodiments, in addition to removing dirt and oil from the skin, the cleanser also reduces the skin bacterial count. Such anti microbial or antibiotic cleanser include an antimicrobial or antibiotic compound. The antimicrobial or antibiotic compounds employed in the cleanser are not particularly limited. Examples of such antimicrobial or antibiotic compounds include, but are not limited to: chlorohexidine gluconate, quaternary ammonia type compounds, alcohol based cleansers (ethanol, isopropyl alcohol, etc., triclosan, zinc pyrithione, sodium sulphacetamide, clindamycin phosphate, and the like. It is envisioned that one or more antimicrobial agents may be used.

In embodiments, one suitable foaming gel cleanser contains a combination of water, cocamidopropyl betaine, sodium lauroyl oat amino acids, sodium laureth sulfate, glycerin, aloe barbadensis gel, glycerth-7, apricot triethanolamine, sage extract, borage extract, phenoxythanol, methylparaben, propylparaben, ethylparaben, butylparaben, saponins, fragrance, and colorant.

After use of the cleanser, a composition containing a polymetal complex may be applied to the cleansed skin of the person afflicted with rosacea. In embodiments, the composition containing a polymetal complex is a moisturizing composition. Generally, the moisturizer may include water, skin conditioners, humectants, minerals, moistening agents, vitamins and complexes thereof, anti-microbials, cleansers, extracts, surfactants, anti-irritants, fragrances and colorants.

Optionally, prior to application of the composition containing a polymetal complex, a composition containing metronidazole is applied to the cleansed skin of the person afflicted with rosacea.

Metronidazole is a nitroimidazole used in the treatment of infections caused by susceptible organisms, particularly anaerobic bacteria and protozoa. Metronidazole is a prodrug. It is converted in anaerobic organisms by the redox enzyme pyruvate-ferredoxin oxidoreductase. The nitro group of metronidazole is chemically reduced by ferredoxin (or a ferredoxin-linked metabolic process) and the products are responsible for disrupting the DNA helical structure, thus inhibiting nucleic acid synthesis. Metronidazole is selectively taken up by anaerobic bacteria and sensitive protozoal organisms because of the ability of these organisms to reduce metronidazole to its active form intracellularly.

The composition containing metronidazole can be formulated in any manner to provide delivery of the active to the skin of a patient afflicted with rosacea. In embodiments, the composition containing metronidazole contains from about 0.001 to about 5 percent metronidazole by weight of the composition, in embodiments from about 0.1 to about 3 percent metronidazole by weight of the composition, in other embodiments in embodiments from about 0.5 to about 1.5 percent metronidazole by weight of the composition.

Metronidazole is commercially available as a gel preparation for the treatment of dermatological conditions such as rosacea. Illustrative commercially available compositions containing metronidazole are available under the tradename METROGEL® from Galderma Laboratories, Fort Worth, Tex. USA. In fact, METROGEL is available from Galderma Laboratories in a kit with a gentle skin cleanser commercially available under the tradename CETAPHIL®.

Optionally, after application of the composition containing a polymetal complex, an anti-redness composition may be applied. The anti-redness composition is a composition containing one or more ingredients that result in redness reduction of the skin, either via a clinical and/or visual manner. The anti-redness composition may include botanicals, calming agents, anti-microbial agents, anti-inflammatory compounds, anti-oxidants, antiseptics, conditioning agents, light refracting materials and the like. Non-limiting examples of such ingredients include Aloe Barbadensis Leaf juice, Hydrolyzed Oat Protein, Bisabolol, Allantoin, *Avena Sativa* (Oat) Beta Glucan, *Avena Sativa* (Oat), Kernel Extract, *Glycyrrhiza Glabra* root extract, Sea Whip Extract, Mica, Titanium Dioxide, Iron Oxides, *Bacopa Monniera* Extract, *Arnica Montana* (Flower) Extract, *Cupressus Sempervirens* (Seed) Extract, *Polygontum Multiflorum* Extract, Sodium Cocoyl Amino Acid, Sarcosine, Potassium Aspartate, Magnesium Aspartate, *Lavandula Angustifolia* (Lavender) Flower/leaf Stem Extract, and Malonic Acid.

An anti-redness composition suitable for use in the presently described regimen is prepared having the composition shown in Table B. The composition is prepared by combining the Water Phase ingredients in a reaction vessel with heating to 70-75° C. and stirring. The Oil Phase ingredients are combined in a separate reaction vessel with heating to 70-75° C. and stirring. The Oil Phase is then added to the Water Phase with continued stirring until a homogenous dispersion is achieved. The Additional Ingredients are then added with stirring.

TABLE B

| Ingredients | Percent | INCI Names | Functionality |
|---|---|---|---|
| Water Phase | | | |
| Distilled Water | 54.08 | Water | Solvent, Moisturizer |
| Phenonip | 1.00 | Phenoxyethanol, Methylparaben, Ethylparaben, Butylparaben, Propylparaben, Isobutylparaben | Preservative |
| Carbowax 300 | 2.25 | PEG-6 | Humectant, solvent |
| Glycerin | 0.50 | Glycerin | Humectant, skin conditioner |
| Di-Propylene Glycol | 2.25 | Dipropylene Glycol | Humectant, solvent |
| Keitrol CG | 0.25 | Xanthan Gum | Suspending agent thickener |
| Veegum | 0.15 | Magnesium Aluminum Silicate | Suspending agent, thickener |
| Oil Phase | | | |
| Pelemol OP | 2.75 | Ethylhexyl Palmitate | Emollient |
| Pelemol ICB | 1.50 | Isocetyl Behenate | Emollient |
| Cetiol LC | 2.75 | Coco-Caprylate/Caprate | Emollient |
| Permethyl 101A | 4.50 | Isohexadecane | Emollient |
| Gemseal 25 | 1.00 | C13-15 Alkane | Emollient |
| Lipomulse 165 | 2.50 | Glyceryl Stearate, PEG 100 Stearate | Emulsifier |
| Cetyl Alcohol | 0.50 | Cetyl Alcohol | Thickener, emulsion stabilizer |
| Stearyl Alcohol | 1.50 | Stearyl Alcohol | Thickener, emulsion stabilizer |
| GE Silcone 98-100 | 1.00 | Dimethicone | Skin Protectant |
| Vitamin E Acetate | 0.05 | Tocopheryl Acetate | Anti-Oxidant |
| Titanium Dioxide MT-500B | 5.00 | Titanium Dioxide | Opacyfing and covering agent |
| Coveleaf AR 80 | 2.00 | Talc, Titanium Dioxide, Alumina, Silica | Soft focus characteristic |
| Simulgel INS 100 | 2.00 | Hydroxyethyl Acrylate/Sodium Acryloldirmethyl Tauarte Copolymer, Isohexadecane, Polysorbate 60 | Emulsifier, thickener |
| Additional Ingredients | | | |
| Soft Tex Yellow Iron Oxide C337773 | 0.03 | Iron Oxide | Tinting/coloring ingredient |
| Soft Tex Red Iron Oxide C337775 | 0.03 | Iron Oxide | Tinting/coloring ingredient |
| Soft Tex Black Iron Oxide 0337734 | 0.02 | Iron Oxide | Tinting/coloring ingredient |
| Water | 3.00 | Water | Solvent, moisturizer |

After use of the polymetal complex moisturizer, a protective composition may be applied to the skin of the person afflicted with rosacea. Suitable protective compositions include any composition capable of reducing skin damage, darkening, or dryness. In embodiments, protective compositions include sun block or sunscreen to filter out ultraviolet light rays. In embodiments, suitable protective compositions include creams that are moisturizers formulated to help control dryness. In embodiments, the protective composition includes at least one of the following compounds: ZnO, Vitamin A, Vitamin D and combinations thereof. Optionally, an anti-parasitic product may also be applied for more severe cases for control of Dermodex mites.

A protective composition suitable for use in the presently described regimen is prepared having the composition shown in Table C. The composition is prepared by combining the Water Phase ingredients in a reaction vessel with heating to 70-75° C. and stirring. The oil phase ingredients are combined in a separate reaction vessel with heating to 70-75° C. and stirring. The oil phase is then added to the water phase with continued stirring until a homogenous dispersion is achieved. The additional ingredients are then added with stirring.

In embodiments, an anti parasitic product may also be applied. An anti parasitic product includes an anti-parasitic compound (such as, for example, pediculicidal or miticidal compounds) that eradicate organisms (such as, for example, ectoparasites (e.g., demodex follicular mites) or endoparasites) that inhabit hair follicles and/or the pores of the skin. Any conventional anti-parasitic compound may be employed. Non-limiting examples of suitable pediculicidal agents include natural or other pyrethrins, pyrethroids, permethrin, lindane, malathion, carbaryl, ivermectin and combinations thereof. Suitable miticides are represented by propynyl sulfites, triazapentadienes, chlorinated aromatics and dinitrophenols. In embodiments, the anti parasitic product may include a combination of benzyl benzoate, and salicylic acid, a combination effective in eradicating skin parasites. Products including anti-parasitic compounds may be particularly useful in regimens for patients having stage two, stage three and stage four rosacea.

Depending upon the severity of the rosacea, it may be desirable to apply an anti-acne medication to the afflicted skin following the application of the polymetal complex moisturizer. Some examples of useful anti-acne medications include, but are not meant to be limited to, benzoyl peroxide,

TABLE C

| Ingredient | Percent | INCI Name | Functionality |
|---|---|---|---|
| Aqueous Phase | | | |
| Water | 50.0550 | Water | Solvent, moisturizer |
| Glycerin | 0.5000 | Glycerin | Humectant, skin conditioner |
| Dipropylene Glycol | 10.0000 | Dipropylene Glycol | Humectant, solvent |
| CARBOWAX 300 ® | 3.0000 | PEG-6 | Humectant, solvent |
| PHENONIP ® | 1.0000 | Phenoxyethanol, Methylparaben, Propypylparaben, Ethylparaben, Butylparaben, Isobutylparaben | Preservative |
| Oil Phase | | | |
| MONTONOV ® 82 | 2.0000 | Cetearyl Alcohol, Cocoa Glucoside | |
| PERMETHYL 101A ® | 0.3000 | Isohexadecane | Emollient |
| KOBO TNP50zSl 11.28% Zinc Oxide (47%) | 24.0000 | C12-15 Alkyl Benzoate, Zinc Oxide, Polyhydroxystearic Acid, Triethoxycaprylsilane | Sunscreen |
| Vitamin E Acetate | 0.0500 | Tocopheryl Acetate | Anti-oxidant |
| Z COTE ® 4.5% Zinc oxide | 4.5000 | Zinc Oxide | Sunscreen, Skin Protectant |
| Micro Titanium Dioxide MT 500B | 1.8000 | Titanium Dioxide | Sunscreen |
| Kobo TNP40VTTS 0.32% Titanium Dioxide (32%) | 1.0000 | C 12-15 Alkyl Benzoate, Titanium Dioxide, Alumina, Polyhydroxystearic Acid, Isopropyl Titanium Triisostearate/ Triethoxycaprylysilane Crosspolymer | Sunscreen |
| Additional Ingredients | | | |
| Flamenco satin Green 860 M | 0.2500 | Mica, Titanium Dioxide, Iron Oxides | Helps to diminish skin redness |
| Soft tex Yellow Iron Oxide C337773 | 0.0200 | Iron Oxides | Tinting masstone |
| Soft tex Red Iron Oxide 0337775 | 0.0150 | Iron Oxides | Tinting masstone |
| Soft tex Black Iron Oxide C337734 | 0.0100 | Iron Oxides | Tinting masstone |
| Sepinov EMT 10 | 1.5000 | Hydroxyethylacrylate/ Sodium Acrylolyldimethyl Taurate | Emulsifier | antibiotics, retinoids, and combinations thereof. In embodiments, compositions containing benzoyl peroxide may be applied to the afflicted area prior to application of the protective compound. This may further reduce the popular and pustular lesions. Suitable benzoyl peroxide compositions may contain, for example, from about one percent to about ten percent by weight benzoyl peroxide.

In other embodiments it may be desirable to apply a composition containing a retinoid to the afflicted area after application of the protective compound. The term retinoid is intended to embrace any compound that binds to or otherwise interacts with a retinoid receptor. Suitable retinoids include retinol, retinoic acid, retinyl palmitate, retinyl propionate, retinyl acetate, tretinoin, isotretinoin, motretinide, adapalene, tazarotene, azelaic acid as well as synthetic retinoid mimetics.

Although not wishing to be bound by this disclosure, it is believed that tretinoin passes through the skin cell membranes to the nucleus wherein it binds to nuclear receptors and regulates transcription of genes that mediate the rate of cell division and turnover, cell differentiation and formulation of new healthy collagen and the repair of elastin. As a result skin can be firmer from the collagen formation as well as more flexible from the repair of elastin.

Tretinoin also increases the formation of normal keratinocytes (cells making up about 90% of the epidermis) and fibroblasts (connective tissue cells which secrete an extracellular matrix rich in collagen and other macromolecules), decreases melanocyte activity (which offers better resistance to external injury and inflammation) and is found to improve angiogenesis (the formation of new blood vessels that increase skin circulation).

In still other embodiments, it also may be desirable to apply a composition containing antibiotic to the afflicted area after application of the protective compound. Any antibiotic known to have a beneficial effect upon the skin may be employed. In embodiments, the antibiotic used is clindamycin, tetracycline, erythromycin or combinations thereof. The antibiotic may be applied topically to the afflicted skin or administered in another manner, such as orally to the subject suffering from rosacea.

The various products applied in a regimen in accordance with the present disclosure can be in the form of solutions, emulsions (including microemulsions), suspensions, creams, lotions, gels, powders, or other typical solid or liquid compositions used for treatment of age related skin conditions. Such compositions may contain, in addition to the specific active(s) identified herein for each product, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

As the rosacea treatment regimens described herein require the sequential application of various components, it has also been found that kits greatly facilitate the user in performing the treatment regimen consistently. One suitable kit for rosacea treatment includes the following:

A cleanser
A composition containing a polymetal complex
A protective composition
Sunscreen with ZnO and vitamins A and D
Optionally one or more of:

Benzoyl Peroxide Composition
Retinoid Composition
Antibiotic Composition
composition containing metronidazole In other embodiments, the kit contains:

A cleanser
A composition containing a polymetal complex
A composition containing metronidazole
An anti-redness composition
A protective composition Optionally one or more of:

In yet other embodiments, the kit contains:

Antimicrobial containing cleanser
Product containing anti-parasitic compounds
Moisturizer with Cu/Zn malonate
Sunscreen with ZnO and vitamins A and D
Optionally one or more of:

Benzoyl Peroxide Composition
Retinoid Composition
Antibiotic Composition

Typically, kits are provided with instructions for care. For example, the instructions may direct that the various compositions of the pre-procedure treatment regimen be applied as follows:

| Rosecea type | Product 1 | Product 2 | Product 3 | Product 4 | Product 5 |
|---|---|---|---|---|---|
| Type 1 (mild) | cleanser | Moisturizer with Cu/Zn malonate | Sunscreen based on ZnO and Vitamin A&D | | |
| Type 2 (moderate) | cleanser | Moisturizer with Cu/Zn malonate | Sunscreen based on ZnO and Vitamin A&D | Anti parasitic product 1% BPO lotion | Retinoic acid |
| Type 3 (severe) | cleanser | Moisturizer with Cu/Zn malonate | Sunscreen based on ZnO and Vitamin A&D | Anti parasitic product 1% BPO lotion | Oral minocycline or tetracycline antibiotic |

In embodiments, a regimen in accordance with the present disclosure is as follows:

| AM | PM |
|---|---|
| Gentle Cleanser | Gentle Cleanser |
| Metronidazole Gel 0.75% | Metronidazole Gel 0.75% |
| Moisturizer with Cu/Zn malonate | Moisturizer with Cu/Zn malonate |
| Anti-Redness Composition (Hydrating Complexion Corrector) | Anti-Redness Composition (Hydrating Complexion Corrector) |
| Skin Balancing Sun Protection SPF 30 | |

The rosacea treatment regimen involves applying designated products in the smallest possible amount sufficient to cover at least a portion of the site afflicted with rosacea. In embodiments, the designated products may also be applied to the entire face of the patient even if only a small area of the face is afflicted with rosacea.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A treatment regimen comprising:
   an A.M. treatment regimen comprising the steps of: (1) cleansing an area of skin afflicted with rosacea with an antimicrobial or antibiotic cleanser; (2) applying to the cleansed area a moisturizing composition, wherein the moisturizing composition comprises a Cu/Zn malonate complex; (3) applying an anti-redness composition to the cleansed and Cu/Zn malonate-treated area; and (4) applying to the cleansed and Cu/Zn malonate-treated area a protective composition, wherein the protective composition comprises a sunscreen; and
   a P.M. treatment regimen comprising the steps of (1) cleansing an area of skin afflicted with rosacea with an antimicrobial or antibiotic cleanser; (2) applying to the cleansed area a moisturizing composition, wherein the moisturizing composition comprises a Cu/Zn malonate complex, and (3) applying an anti-redness composition to the cleansed and Cu/Zn malonate-treated area; wherein the P.M. treatment regimen does not comprise applying a protective composition comprising a sunscreen.

2. The treatment regimen of claim 1, wherein for either or both of the A.M. treatment regimen or the P.M. treatment regimen, prior to the step of applying the composition comprising the Cu/Zn malonate complex, the regimen further comprises applying a composition containing metronidazole to the cleansed area.

3. The treatment regimen of claim 1, wherein in the A.M. treatment regimen subsequent to the step of applying the protective composition, the regimen further comprises applying an anti-parasitic compound to the cleansed, Cu/Zn malonate-treated, and protective composition-treated area.

4. The treatment regimen of claim 3 wherein the anti-parasitic product is selected from the group consisting of benzyl benzoate, salicylic acid and combinations thereof.

5. The treatment regimen of claim 1, wherein the moisturizing composition comprises Cu/Zn malonate complex in an amount from about 0.001 to about 5% by weight of the total composition.

6. The treatment regimen of claim 1 wherein the protective composition comprises a compound selected from the group consisting of ZnO, Vitamin A, Vitamin D and combinations thereof.

7. The treatment regimen of claim 1, wherein in the A.M. treatment regimen subsequent to the step of applying the protective composition, the regimen further comprises applying a benzoyl peroxide containing composition to the cleansed, Cu/Zn malonate-treated, and protective composition-treated area.

8. The treatment regimen as in claim 1, wherein in the A.M. treatment regimen subsequent to the step of applying the protective composition, the regimen further comprises applying a retinoid containing composition to the cleansed, Cu/Zn malonate-treated, and protective composition-treated area.

9. The treatment regimen as in claim 1, wherein in the A.M. treatment regimen subsequent to the step of applying the protective composition, the regimen further comprises applying an antibiotic containing composition to the cleansed, Cu/Zn malonate-treated, and protective composition-treated area.

10. The treatment regimen of claim 1, wherein in the A.M. treatment regimen subsequent to the step of applying the protective composition, the regimen further comprises taking an oral antibiotic.

11. A kit comprising:
    a first composition, wherein the first composition is a cleanser, wherein the cleanser comprises an antimicrobial or antibiotic compound;
    a second composition, wherein the second composition is a moisturizing composition comprising a Cu/Zn malonate complex;
    a third composition, wherein the third composition is a protective composition comprising a sunscreen;
    a fourth composition, wherein the fourth composition is a composition containing metronidazole; and
    a fifth composition, wherein the fifth composition is an anti-redness composition.

12. The kit of claim 11 further comprising a composition containing an anti-acne medication.

13. The kit of claim 11 further comprising an anti-parasitic composition.

14. The kit of claim 11 wherein the moisturizing composition comprises Cu/Zn malonate complex in an amount from about 0.001 to about 5% by weight of the total composition.

15. The kit of claim 11 wherein the protective composition comprises ZnO, vitamin A, vitamin D or combinations thereof in a dermatologically acceptable carrier.

16. The kit of claim 11 wherein the cleanser is an antimicrobial cleanser.

17. The kit of claim 16 wherein the antimicrobial cleanser is selected from the group consisting of chlorhexidine gluconate, triclosan, zinc pyrithione, clindamycin phosphate, sodium sulphacetamide and combinations thereof.

18. The kit of claim 11 wherein the anti-redness composition includes a compound selected from the group consisting of bisabolol, *glycyrrhiza glabra* root extract, sea whip extract, *bacopa monniera* extract, sodium cocoyl amino acids, *lavandula angustifolia* (lavender) flower/leaf stem extract, aloe barbadensis leaf juice, hydrolyzed oat protein, allantoin, *avena sativa* (oat) beta glucan, *avena sativa* (oat) kernel extract, *arnica montana* extract, *cupressus sempervirens* extract, *polygontum multiflorum* extract, sarcosine, potassium aspartate, magnesium aspartate, and combinations thereof, in a dermatologically acceptable carrier.

19. The kit of claim 12 wherein the anti-acne medication is selected from the group consisting of benzoyl peroxide, antibiotics, retinoids, and combinations thereof.

20. The kit of claim 13 wherein the anti-parasitic product includes a compound selected from the group consisting of benzyl benzoate, salicylic acid and combinations thereof.

* * * * *

UNITED STATES PATENT AND TRADEMARK OFFICE
CERTIFICATE OF CORRECTION

PATENT NO. : 9,629,789 B2  
APPLICATION NO. : 14/026592  
DATED : April 25, 2017  
INVENTOR(S) : Joseph R. Faryniarz, Jose E. Ramirez and Hovig Ounanian Page 1 of 1

It is certified that error appears in the above-identified patent and that said Letters Patent is hereby corrected as shown below:

On the Title Page

In Column 1, in item (72), in "Inventors", Line 3, delete "Hovig Ounian" and insert -- Hovig Ounanian --, therefor.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*